US012685514B2

(12) United States Patent
Nachtomy et al.

(10) Patent No.: US 12,685,514 B2
(45) Date of Patent: Jul. 21, 2026

(54) INTRALUMINAL AND EXTRALUMINAL IMAGE REGISTRATION

(71) Applicant: KONINKLIJKE PHILIPS N.V., Eindhoven (NL)

(72) Inventors: Ehud Nachtomy, Herzliya (IL); Michael Zarkh, Qiryat Ono (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 87 days.

(21) Appl. No.: 18/275,104

(22) PCT Filed: Jan. 14, 2022

(86) PCT No.: PCT/EP2022/050719
§ 371 (c)(1),
(2) Date: Jul. 31, 2023

(87) PCT Pub. No.: WO2022/161790
PCT Pub. Date: Aug. 4, 2022

(65) Prior Publication Data
US 2024/0090876 A1     Mar. 21, 2024

(30) Foreign Application Priority Data
Feb. 1, 2021     (EP) ..................................... 21154591

(51) Int. Cl.
*A61B 8/00*          (2006.01)
*A61B 6/12*          (2006.01)
(Continued)

(52) U.S. Cl.
CPC .............. *A61B 8/5261* (2013.01); *A61B 6/12* (2013.01); *A61B 8/12* (2013.01); *A61B 34/20* (2016.02); *A61B 2034/2065* (2016.02)

(58) Field of Classification Search
CPC .......... A61B 8/5261; A61B 8/12; A61B 34/20
See application file for complete search history.

(56) References Cited

U.S. PATENT DOCUMENTS

2010/0094124 A1     4/2010     Schoonenberg
2013/0184571 A1*    7/2013     Wilkening ............. A61B 90/39
                                                       600/426
(Continued)

FOREIGN PATENT DOCUMENTS

EP          2873371 A1     5/2015

OTHER PUBLICATIONS

International Search Report and Written Opinion of PCT/EP2022/050719, dated Apr. 4, 2022.
(Continued)

*Primary Examiner* — Rochelle D Turchen

(57) ABSTRACT

Systems and computer-implemented methods of registering positions of a temporal sequence of intraluminal sensing device data ($101_{1 \ldots m}$) to positions along a guidewire (104) in a temporal sequence of extraluminal image frames ($105_{1 \ldots n}$) include: determining (S120) a position of a sensing portion (106) of the intraluminal sensing device (102) along the guidewire (104), based on a matching of image intensity values determined at positions along the guidewire (104) in the extraluminal image frame ($105_{1 \ldots n}$), with an expected intensity pattern (107) representing a portion of the intraluminal sensing device (102); and mapping (S130) a position of an intraluminal sensing device data ($101_{1 \ldots m}$) generated contemporaneously with the extraluminal image frame ($105_{1 \ldots n}$), to the determined position along the guidewire (104).

14 Claims, 5 Drawing Sheets

Identifying guidewire in X-ray image frame S110

Determining position of imaging portion of IVUS imaging device along guidewire S120

Mapping position of IVUS image frame to determined position along guidewire S130

(51) Int. Cl.
    *A61B 8/12*            (2006.01)
    *A61B 34/20*         (2016.01)

(56)                 References Cited

U.S. PATENT DOCUMENTS

| | | | |
|---|---|---|---|
| 2016/0007947 A1* | 1/2016 | Spencer | A61B 8/0841 |
| | | | 600/424 |
| 2018/0008222 A1* | 1/2018 | Chen | G06T 7/73 |
| 2018/0296117 A1* | 10/2018 | Sra | A61B 6/485 |

OTHER PUBLICATIONS

Vandini, Alessandro. et al "Robust Guidewire Tracking under Large Deformations Combining Segment-Like Features (SEGlets)", Medical Image Analysis, vol. 38, pp. 150-165, 2017.
Ambrosini, Pierre et al "Fully Automatic and Real-Time Catheter Segmentation in X-Ray Fluoroscopy", Medical Image Computing and Computer-Assisted Intervention—MICCAI 2017, pp. 577-585. vol. 10434.

\* cited by examiner

INTRALUMINAL AND EXTRALUMINAL IMAGE REGISTRATION

CROSS-REFERENCE TO PRIOR APPLICATIONS

This application is the U.S. National Phase application under 35 U.S.C. § 371 of International Application No. PCT/EP2022/050719, filed on Jan. 14, 2022, which claims the benefit of European Patent Application No. 21154591.8, filed on Feb. 1, 2021. These applications are hereby incorporated by reference herein.

TECHNICAL FIELD

The present disclosure relates to computer-implemented methods of registering positions of a temporal sequence of intraluminal image frames in a temporal sequence of extraluminal image frames. Related computer program product, computer-readable storage medium, and systems, are also disclosed.

BACKGROUND

Interventional medical procedures are often performed under X-ray imaging. Intravascular ultrasound "IVUS" imaging is often used in combination with X-ray imaging in order to augment the anatomical information provided by X-ray images. For example, peripheral venous interventions are often performed using under a combination of X-Ray imaging, and IVUS imaging. In such procedures, a guidewire is typically inserted into the vasculature under X-ray guidance, and an IVUS imaging device is translated along the guidewire during a procedure termed "pullback". The information obtained from the IVUS imaging procedure is used to evaluate tissue properties within the vasculature, and the information from the X-ray imaging procedure is used to navigate the IVUS imaging device within the vasculature. The combination of X-ray and IVUS imaging may therefore be used to evaluate the presence of disease or deformities, e.g. venous compression, within the vasculature, or to plan or carry out an intervention within the vasculature such as the insertion of a balloon, or a stent, and so forth.

A challenge faced by medical practitioners when performing interventional procedures that involve both X-ray and IVUS imaging, is to determine the position of the IVUS imaging device at which its images were generated, within the vasculature in the X-ray images. At present, a medical practitioner may perform this task by visually associating the position of the IVUS imaging device within the vasculature, as seen in the X-ray image, with the live ultrasound images that are generated by the IVUS imaging device. Under the current workflow, the medical practitioner typically performs an IVUS pullback procedure, and then reviews the resulting IVUS images. In order to confirm the position of any IVUS images of interest within the vasculature, the medical practitioner may then re-insert the IVUS imaging device into the vasculature under live X-ray guidance.

Another challenge faced by medical practitioners when performing interventional procedures that involve both X-ray and IVUS imaging, is to determine measurements in the X-ray images. The measurements may for example be used to specify the dimensions of a stent to be used in a stenting procedure. A required diameter of the stent may be determined from the IVUS image data. However, it can be more challenging to accurately determine the required length of the stent, and also to do this in a time-efficient manner. Effects such as foreshortening in the X-ray images preclude the use of a uniform scale for an X-ray image. An approximation of the required length of stents that are used in peripheral venous interventions, is sometimes determined by counting the number of radiopaque fiducial markers disposed along the sheath of the IVUS imaging catheter. However, manually counting the number of markers is laborious since some catheters include twenty or more markers.

Thus, there remains room for improvements when IVUS imaging is performed in combination with X-ray imaging.

SUMMARY

According to an aspect of the present invention a system is disclosed for registering positions of a temporal sequence of intraluminal sensing device data generated by an intraluminal sensing device coupled to a guidewire, to positions along the guidewire in a temporal sequence of extraluminal image frames including the intraluminal sensing device and the guidewire, the system comprising one or more processors configured to perform a method comprising: for a plurality of extraluminal image frames in the temporal sequence:

identifying the guidewire in the extraluminal image frame;

determining a position of a sensing portion of the intraluminal sensing device along the guidewire, based on a matching of image intensity values determined at positions along the guidewire in the extraluminal image frame, with an expected intensity pattern representing a portion of the intraluminal sensing device; and mapping a position of an intraluminal sensing device data generated contemporaneously with the extraluminal image frame, to the determined position along the guidewire.

In an embodiment, determining the position of the sensing portion of the intraluminal sensing device along the guidewire, is based on matching of image intensity values determined at positions along the guidewire in the extraluminal image frame, with the expected intensity pattern representing the sensing portion of the intraluminal sensing device.

In some of the embodiments, the temporal sequence of intraluminal sensing device data comprises temporal sequence of intraluminal ultrasound image frames.

In some of the embodiments, the intraluminal ultrasound image frames comprise intravascular ultrasound image frames or endobronchial ultrasound image frames.

In some of the embodiments, the extraluminal image frames comprise radiographic image frames.

In an aspect of the invention a computer-implemented method is presented, of registering positions of a temporal sequence of intraluminal sensing device data generated by an intraluminal sensing device coupled to a guidewire, to positions along the guidewire in a temporal sequence of extraluminal image frames including the intraluminal sensing device and the guidewire, the method comprising, for a plurality of extraluminal image frames in the temporal sequence:

identifying the guidewire in the extraluminal image frame;

determining a position of a sensing portion of the intraluminal sensing device along the guidewire, based on a matching of image intensity values determined at positions along the guidewire in the extraluminal image frame, with an expected intensity pattern representing a portion of the intraluminal sensing device; and mapping a position of an intraluminal sensing device data generated contemporaneously with the extraluminal image frame, to the determined position along the guidewire.

In some of the embodiments, determining the position of the sensing portion of the intraluminal sensing device along the guidewire, is based on matching of image intensity values determined at positions along the guidewire in the extraluminal image frame, with the expected intensity pattern representing the sensing portion of the intraluminal sensing device, wherein the temporal sequence of intraluminal sensing device data comprises temporal sequence of intraluminal ultrasound image frames provided by an intravascular imaging device or endobronchial imaging device wherein the extraluminal image frames comprise radiographic image frames.

According to an embodiment of the present disclosure, a computer-implemented method is presented, of registering positions of a temporal sequence of intravascular ultrasound, IVUS, image frames generated by an IVUS imaging device coupled to a guidewire, to positions along the guidewire in a temporal sequence of X-ray image frames including the IVUS imaging device and the guidewire, is disclosed. The method includes, for a plurality of X-ray image frames in the temporal sequence:

identifying the guidewire in the X-ray image frame;

determining a position of an imaging portion of the IVUS imaging device along the guidewire, based on a matching of image intensity values determined at positions along the guidewire in the X-ray image frame, with an expected intensity pattern representing the IVUS imaging device; and mapping a position of an IVUS image frame generated contemporaneously with the X-ray image frame, to the determined position along the guidewire.

In some of the embodiments, the matching of image intensity values determined at positions along the guidewire in the X-ray image frame, with an expected intensity pattern representing the IVUS imaging device, comprises:

determining the image intensity values at the positions along the guidewire in the X-ray image frame by sampling the image intensity values within a window extending transversally with respect to the guidewire to provide a composite value for the window, at each position; and comparing the composite values determined at the positions along the guidewire, with the expected intensity pattern representing the IVUS imaging device, and wherein the expected intensity pattern comprises an expected profile of the composite values along the length of the guidewire.

In some of the embodiments, the determining a position of an imaging portion of the IVUS imaging device along the guidewire, comprises translating the expected intensity pattern representing the IVUS imaging device along the guidewire in the X-ray image frame in order to determine a position at which the image intensity values in the X-ray image frame, match the expected intensity pattern representing the IVUS imaging device.

In some of the embodiments, the translating the expected intensity pattern representing the IVUS imaging device along the guidewire in the X-ray image frame in order to determine a position at which the image intensity values in the X-ray image frame, match the expected intensity pattern representing the IVUS imaging device, comprises:

performing an initial translation of the expected intensity pattern representing the IVUS imaging device along the guidewire in the X-ray image frame by sampling the image intensity values in the X-ray image frame with a first spatial resolution, to determine a first estimated position of the imaging portion of the IVUS imaging device along the guidewire;

estimating a scale factor for at least a portion of the IVUS imaging device based on the sampled image intensity values and a known dimension of the portion of the IVUS imaging device; and performing a subsequent translation of the expected intensity pattern representing the IVUS imaging device along the guidewire in the X-ray image frame by sampling the image intensity values in the X-ray image frame with a second spatial resolution, to determine a second estimated position of the imaging portion of the IVUS imaging device along the guidewire, the second spatial resolution being adjusted based on the estimated scale factor; and using the second estimated position as the determined position of the imaging portion of the IVUS imaging device along the guidewire.

In some of the embodiments, the IVUS imaging device comprises a plurality of fiducial markers;

wherein the fiducial markers are coupled to the IVUS imaging device and are distributed axially along the guidewire; and wherein the determining a position of an imaging portion of the IVUS imaging device along the guidewire, comprises:

identifying positions of the fiducial markers along the guidewire by sampling the image intensity values in the X-ray image frame with a first spatial resolution;

computing an estimated separation between at least one pair of the fiducial markers based on the identified positions of the fiducial markers; and sampling the image intensity values in the X-ray image frame with a second spatial resolution, to determine a position at which the image intensity values in the X-ray image frame, match the expected intensity pattern representing the IVUS imaging device, and wherein the second spatial resolution is determined based on the estimated separation between at least one pair of the fiducial markers and a known separation between the at least one pair of the fiducial markers.

In some of the embodiments, the method is further comprising:

generating a template pattern representing an imaging portion of the IVUS imaging device by averaging the image intensity values surrounding the determined position of the imaging portion of the IVUS imaging device in the plurality of X-ray image frames; and repeating the determining a position of an imaging portion of the IVUS imaging device along the guidewire for the plurality of X-ray image frames, using the template pattern as the expected intensity pattern representing the IVUS imaging device, to provide an adjusted position of the imaging portion of the IVUS imaging device along the guidewire in each X-ray image frame.

In some of the embodiments, the IVUS imaging device comprises a radiopaque material, and wherein the expected intensity pattern representing the IVUS imaging device comprises an X-ray attenuation pattern of the radiopaque material extending along an axial and/or a radial direction with respect to the guidewire.

In some of the embodiments, the IVUS imaging device comprises a catheter having a shaft and a plurality of fiducial markers, and wherein the fiducial markers are coupled to the catheter, and distributed axially along the shaft of the catheter.

In some of the embodiments, the method is further comprising:

identifying the plurality of fiducial markers in the X-ray image frame; and determining a scale factor for the portion of the guidewire including the fiducial markers based on a measured separation between two or more of the plurality of fiducial markers identified in the X-ray image frame and a known separation between the two or more fiducial markers.

In some of the embodiments, the IVUS imaging device is translated along the guidewire between successive X-ray image frames in the temporal sequence, and wherein the scale factors for the portion of the guidewire including the fiducial markers in each image frame, are combined for corresponding sections of the guidewire in the X-ray image frames, to provide a combined scale factor (110) for the guidewire that varies along the length of the guidewire.

In some of the embodiments, the scale factors for the portion of the guidewire including the fiducial markers in each image frame, are combined for corresponding sections of the guidewire in the X-ray image frames by using a regularisation term to encourage a continuous change of scale factor along the length of the guidewire.

In some of the embodiments, the X-ray image frames in the temporal sequence comprise a plurality of guidewires; and wherein the identifying the guidewire in the X-ray image frame, comprises:

identifying the fiducial markers in the X-ray image frame; and selecting the guidewire having the identified fiducial markers distributed axially along its length.

In some of the embodiments, the mapping a position of an IVUS image frame generated contemporaneously with the X-ray image frame, to the determined position along the guidewire, comprises:

displaying a first image representing one or more of the X-ray image frames in the temporal sequence and the guidewire, and simultaneously displaying a second image representing an IVUS image frame from the temporal sequence of IVUS image frames; and indicating the mapped position of the IVUS image frame along the guidewire in the first image.

In an aspect of the present invention a computer program product is presented, comprising instructions which when executed by one or more processors, cause the one or more processors to carry out any of the computer-implemented methods according the embodiments of the invention.

Further aspects, features and advantages of the present disclosure will become apparent from the following description of examples, which is made with reference to the accompanying drawings.

BRIEF DESCRIPTION OF THE DRAWINGS

FIG. 4 illustrates a) image intensities from an X-ray image frame $105_n$ including a guidewire 104 and an IVUS imaging device 102, b) a first example of an expected intensity pattern 107 representing a portion of the IVUS imaging device 102, and c) a second example of an expected intensity pattern 107 representing a portion of the IVUS imaging device 102, in accordance with some aspects of the present disclosure.

FIG. 5 illustrates an example of a template pattern 109 representing an imaging portion 106 of the IVUS imaging device 102, in accordance with some aspects of the present disclosure.

FIG. 6 illustrates an example of an X-ray image frame $105_n$ including a guidewire 104 and a combined scale factor 110 for the guidewire 104 that varies along the length of the guidewire 104, in accordance with some aspects of the present disclosure.

DETAILED DESCRIPTION

Figure 1:
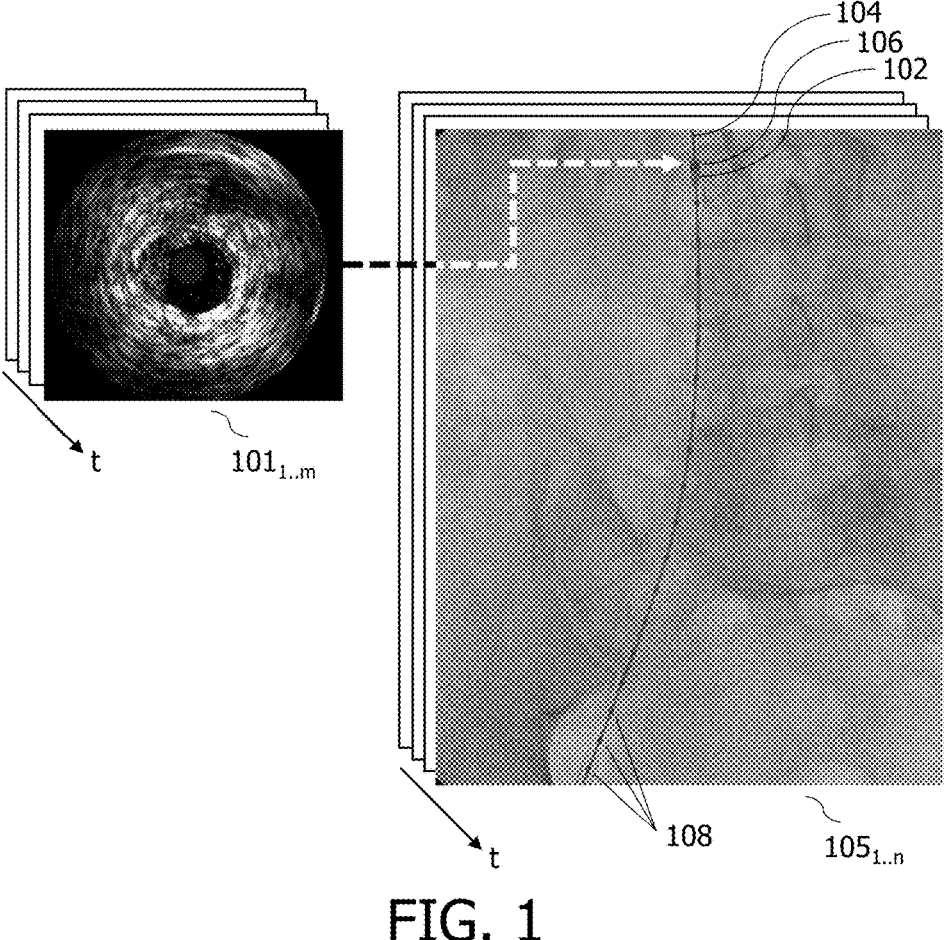
FIG. 1 is a schematic diagram illustrating an example method of registering positions of a temporal sequence of IVUS image frames $101_{1 \ldots m}$ generated by an IVUS imaging device 102 coupled to a guidewire 104, to positions along the guidewire 104 in a temporal sequence of X-ray image frames $105_{1 \ldots n}$, in accordance with some aspects of the present disclosure.

Examples of the present disclosure are provided with reference to the following description and the figures. In this description, for the purposes of explanation, numerous specific details of certain examples are set forth. Reference in the specification to "an example", "an implementation" or similar language means that a feature, structure, or characteristic described in connection with the example is included in at least that one example. It is also to be appreciated that features described in relation to one example may also be used in another example, and that all features are not necessarily duplicated in each example for the sake of brevity. For instance, features described in relation to a computer-implemented method may be implemented in the computer program product, and in the computer-readable storage medium, and in the system, in a corresponding manner.

In the following description, reference is made to computer implemented methods of registering positions of a temporal sequence of IVUS image frames to positions in a temporal sequence of X-ray image frames, that involve imaging an IVUS imaging device within the vasculature using X-ray imaging. It is to be appreciated that the X-ray image frames may be generated from various X-ray imaging procedures that generate a temporal sequence of X-ray image frames. These include, for example, a fluoroscopy imaging procedure, i.e. a live X-ray imaging procedure, and an angiographic or venographic imaging procedure, i.e. a live X-ray imaging procedure that is performed at least in part using a contrast agent. References made herein to the vasculature are intended to encompass both the venous and arterial portions of the vasculature. Although the invention is exemplified with X-ray imaging procedure, it is contemplated that other extracorporeal or intracorporeal imaging devices may be used to provide the extraluminal images, such as magnetic resonance imaging or ultrasound imaging devices (e.g. transthoracic, transesophageal, intracardiac). In some embodiments the positions of a temporal sequence of IVUS image frames are registered to positions in a temporal sequence of image frames of the respective extracorporeal or intracorporeal imagining modalities.

Reference is also made herein to an IVUS imaging procedure that is used to diagnose a portion of the vasculature during a peripheral venous intervention. However, it is to be appreciated that the methods disclosed herein may be used in IVUS imaging procedures in general. The IVUS imaging procedure may be used to perform a diagnosis on another portion of the vasculature, i.e. on another venous or arterial portion of the vasculature. For example, the methods may be used to perform a diagnosis of the coronary arteries in a percutaneous coronary intervention "PCI" procedure, neurovascular procedures, etc. The IVUS images may be alternatively endobronchial ultrasound images obtained with an endobronchial ultrasound imaging device (EBUS) which uses ultrasound to obtain images of internal structures in the airways, the airway walls and the lungs. IVUS and EBUS both provide ultrasound images from a lumen within the body, IVUS from a vascular lumen and EBUS from a lumen of an airway.

Moreover, the methods disclosed herein are not limited to use in diagnostic IVUS imaging procedures, and may be used in IVUS imaging procedures in general, including IVUS imaging procedures that include a treatment of the vasculature. Examples in accordance with the present disclosure may for example be used during a treatment of the peripheral or coronary veins or arteries, as well as during a treatment of other regions of the vasculature. Such treatment procedures may include treatment of the vasculature in the form of the removal of material from the vasculature, the treatment of the vasculature with energy such as light, as well as in procedures that involve the insertion of implantable devices into the vasculature such as a balloon or a stent.

In the description, reference is also made to a method of determining an X-ray image scale factor that varies along an axis of an elongate interventional device. It is to be appreciated that this method is not limited to use in combination with an IVUS imaging procedure. This method may be used in the aforementioned X-ray imaging procedures wherein elongate interventional devices in general, are imaged. The elongate interventional device may for example be a guidewire, a catheter, or another elongate interventional device along which fiducial markers, are translated during a medical intervention. The fiducial markers may be coupled to an IVUS imaging device, or to another device such as an optical coherence tomography "OCT" imaging device, a pressure sensing device, an ICE catheter, a blood flow measurement device, a stent insertion device, or a vascular treatment device such as an atherectomy device, and indeed any elongate interventional device having identifiable parts in the X-ray image that have a known physical dimension along the longitudinal axis of the elongate interventional device. In case that in the system or computer-implemented method other extracorporeal imaging device is used than X-ray based, then the fiducial markers will be from a material that is detectable by the respective imaging modality (e.g. markers for magnetic resonance imaging, echogenic markers for ultrasound). Such markers are known in the art.

It is noted that the computer-implemented methods disclosed herein may be provided as a non-transitory computer-readable storage medium including computer-readable instructions stored thereon which, when executed by at least one processor, cause the at least one processor to perform the method. In other words, the computer-implemented methods may be implemented in a computer program product. The computer program product can be provided by dedicated hardware or hardware capable of running the software in association with appropriate software. When provided by a processor, the functions of the method features can be provided by a single dedicated processor, by a single shared processor, or by a plurality of individual processors, some of which can be shared. The explicit use of the terms "processor" or "controller" should not be interpreted as exclusively referring to hardware capable of running software, and can implicitly include, but is not limited to, digital signal processor "DSP" hardware, read only memory "ROM" for storing software, random access memory "RAM", a non-volatile storage device, and the like. Furthermore, examples of the present disclosure can take the form of a computer program product accessible from a computer usable storage medium or a computer-readable storage medium, the computer program product providing program code for use by or in connection with a computer or any instruction execution system. For the purposes of this description, a computer-usable storage medium or computer-readable storage medium can be any apparatus that can comprise, store, communicate, propagate, or transport a program for use by or in connection with an instruction execution system, apparatus, or device. The medium can be an electronic, magnetic, optical, electromagnetic, infrared, or semiconductor system or device or propagation medium. Examples of computer-readable media include semiconductor or solid-state memories, magnetic tape, removable computer disks, random access memory "RAM", read only memory "ROM", rigid magnetic disks, and optical disks. Current examples of optical disks include compact disk-read only memory "CD-ROM", optical disk-read/write "CD-R/W", Blu-Ray™, and DVD.

As mentioned above, interventional medical procedures are often performed using a combination of IVUS and X-ray imaging. For example, peripheral venous interventions are often performed using under a combination of X-Ray imaging, and IVUS imaging. In such procedures, a guidewire is typically inserted into the vasculature under X-ray guidance, and an IVUS imaging device is translated along the guidewire during a pullback procedure. The information obtained from the IVUS imaging procedure is used to evaluate tissue properties within the vasculature, and the information from the X-ray imaging procedure is used to navigate the IVUS imaging device within the vasculature. However, it can be challenging to determine the position of the IVUS imaging device at which its images were generated, within the vasculature in the X-ray images. Another challenge faced by medical practitioners when performing interventional procedures that involve both X-ray and IVUS imaging, is to determine measurements within the X-ray images. This information may be used in for example determining dimensions of a stent to be used in a stenting procedure. Embodiments of the present disclosure may address one or more of the above challenges.

Figure 2:
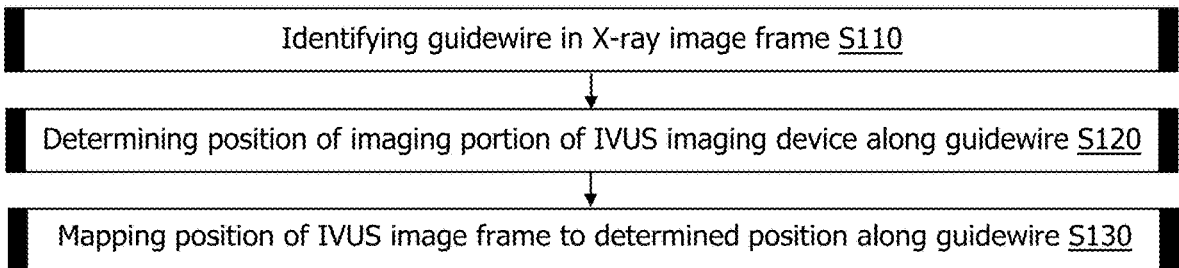
FIG. 2 is a flowchart illustrating an example method of registering positions of a temporal sequence of IVUS image frames $101_{1 \ldots m}$ generated by an IVUS imaging device 102 coupled to a guidewire 104, to positions along the guidewire 104 in a temporal sequence of X-ray image frames $105_{1 \ldots n}$, in accordance with some aspects of the present disclosure.

FIG. 1 is a schematic diagram illustrating an example method of registering positions of a temporal sequence of IVUS image frames $101_{1 \ldots m}$ generated by an IVUS imaging device 102 coupled to a guidewire 104, to positions along the guidewire 104 in a temporal sequence of X-ray image frames $105_{1 \ldots n}$, in accordance with some aspects of the present disclosure. FIG. 2 is a flowchart illustrating an example method of registering positions of a temporal sequence of IVUS image frames $101_{1 \ldots m}$ generated by an IVUS imaging device 102 coupled to a guidewire 104, to positions along the guidewire 104 in a temporal sequence of X-ray image frames $105_{1 \ldots n}$, in accordance with some aspects of the present disclosure.

The temporal sequence of IVUS image frames $101_{1 \ldots m}$ illustrated in FIG. 1 may be generated by an IVUS imaging device IVUS such as the Visions PV.035® catheter that is available from Philips Medical Systems, Best, The Netherlands. Alternatively, the temporal sequence of IVUS image frames $101_{1 \ldots m}$ may be generated by another IVUS imaging device. The temporal sequence of X-ray image frames $105_{1 \ldots n}$ may be generated by an X-ray imaging system such as the Azurion 7 available from Philips Medical Systems, Best, The Netherlands. Alternatively, the temporal sequence of X-ray image frames $105_{1 \ldots n}$ may be generated by another X-ray or CT imaging system.

The temporal sequence of IVUS image frames $101_{1 \ldots m}$ illustrated in FIG. 1 represent the intensity of reflected ultrasound signals measured within the vasculature in a radial direction with respect to the IVUS imaging device. A medical practitioner may study the IVUS image frames $101_{1 \ldots m}$ as part of a clinical investigation for cardiovascular disease. In-use, the IVUS imaging device used to obtain the temporal sequence of IVUS image frames $101_{1 \ldots m}$ is coupled to a guidewire. Peripheral venous procedures often use a 0.035 Radio-Opaque "RO" guidewire. The guidewire permits the IVUS imaging device to be translated along the vasculature. Both the IVUS imaging device 102, and the guidewire 104, are visible in the temporal sequence of X-ray image frames $105_{1 \ldots n}$ illustrated in FIG. 1. The guidewire can be identified as the continuous dark line extending downwards in FIG. 1. The IVUS imaging device includes an imaging portion 106 and a sheath. The imaging portion 106 is located towards the upper section of the guidewire 104 in the displayed X-ray image frames $105_{1 \ldots n}$. The sheath extends downwards from the imaging portion 106 and overlaps the guidewire 104. The sheath includes multiple radiopaque fiducial markers 108 that are distributed axially along the sheath. In FIG. 1, the IVUS imaging device 102 extends over the guidewire, and is coupled to the guidewire such that the IVUS imaging device 102 may be translated, i.e. slide, along the guidewire 102. In the example illustrated in FIG. 1, the guidewire extends through the sheath and also through a bore in the imaging portion 106 of the IVUS imaging device 102. This allows the IVUS imaging device to be translated along the guidewire within the vasculature during insertion and pullback of the IVUS imaging device 102. Other IVUS imaging devices may employ different techniques for coupling the IVUS imaging device 102 to the guidewire 104 such that the IVUS imaging device may be translated along the guidewire during the insertion and pullback operations.

With reference to FIG. 1 and FIG. 2, a computer-implemented method of registering positions of a temporal sequence of intravascular ultrasound, IVUS, image frames $101_{1 \ldots m}$ generated by an IVUS imaging device 102 coupled to a guidewire 104, to positions along the guidewire 104 in a temporal sequence of X-ray image frames $105_{1 \ldots n}$ including the IVUS imaging device 102 and the guidewire 104, comprises, for a plurality of X-ray image frames $105_{1 \ldots n}$ in the temporal sequence:

identifying S110 the guidewire 104 in the X-ray image frame;

determining S120 a position of an imaging portion 106 of the IVUS imaging device 102 along the guidewire 104, based on a matching of image intensity values determined at positions along the guidewire 104 in the X-ray image frame $105_{1 \ldots n}$ with an expected intensity pattern 107 representing the IVUS imaging device 102; and mapping S130 a position of an IVUS image frame $101_{1 \ldots m}$ generated contemporaneously with the X-ray image frame $105_{1 \ldots n}$, to the determined position along the guidewire 104.

With reference to operation S110 in FIG. 2, various techniques may be used to identify S110 the guidewire 104 in the X-ray image frame. Image segmentation techniques may for example be used for this purpose. One example technique is disclosed in a document entitled "Robust guidewire tracking under large deformations combining segment-like features (SEGlets)", by Vandini, A., et al., Medical Image Analysis, Volume 38, pp 150-164. Another example technique that employs a deep convolutional neural network, is disclosed in a document entitled "Fully Automatic and Real-Time Catheter Segmentation in X-Ray Fluoroscopy", by Ambrosini, P. et al., in: Descoteaux, M., et al., (Editors) Medical Image Computing and Computer-Assisted Intervention—MICCAI 2017 pp 577-585. Lecture Notes in Computer Science, vol 10434. Springer, Cham.

With reference to operation S120 in FIG. 2, i.e. determining a position of an imaging portion of the IVUS imaging device along the guidewire, various example techniques are described below.

In general, it is noted that the imaging portion 106 of the IVUS imaging device 102 refers to the region at which ultrasound imaging signals are transmitted and/or received by the IVUS imaging device 102. IVUS imaging devices typically fall into one of two categories depending on whether they employ a rotating imaging transducer, or not. The former group typically includes a single imaging transducer that is rotated circumferentially around the longitudinal axis of the IVUS imaging device whilst transmitting and receiving ultrasound signals. Each revolution of the transducer generates image data, typically in a plane perpendicular to the longitudinal axis. The data from each revolution is typically used in combination with axial position data representing the position of the IVUS imaging device during pullback, to generate volumetric IVUS image data. In IVUS imaging devices that employ a rotational imaging transducer, the position of the imaging portion 106 refers to the position of a circumference around the longitudinal axis of the IVUS imaging device that is intercepted by the ultrasound signals. The latter category typically includes an array of ultrasound imaging transducers. The transducers are typically disposed circumferentially around the longitudinal axis of the IVUS imaging device. These circumferentially-arranged transducers generate image data in a radial direction with respect to the longitudinal axis of the IVUS imaging device without the need for their physical rotation. Ultrasound signals transmitted and received by the array may be steered using beamforming techniques in order to perform imaging in a desired direction. The imaging transducers in this latter group are typically arranged in one or more rows. Other IVUS imaging devices in this latter category employ an array of ultrasound transducers to transmit and receive ultrasound signals in other directions, such as axially within the vasculature. In IVUS imaging devices that do not employ a rotating imaging transducer, the position of the imaging portion 106 refers to the location on the IVUS imaging device, where the ultrasound signals are intercepted.

It is noted that expected intensity pattern 107 representing the IVUS imaging device 102 that is used in operation S120, i.e. in determining a position of an imaging portion of the IVUS imaging device along the guidewire, may be compared with the image intensity values determined at positions along the guidewire 104 in the X-ray image frame $105_{1 \ldots n}$, in order to determine whether a match exists. The comparison may for example include the use of a correlation technique, a trained classifier—for example a support vector machine "SVM", a convolutional neural network—i.e. deep learning techniques, and so forth. The position along the guidewire that has the closest match may then be selected as the position at which the match exists.

In general, the expected intensity pattern 107 may represent a portion of the IVUS imaging device 102. For example, the expected intensity pattern 107 may represent the imaging portion and/or another portion of the IVUS imaging device 102 such as its shaft. The imaging portion of the IVUS imaging device typically includes dense materials such as metals that are detectable in X-ray images. The shaft of the IVUS imaging device 102 typically includes one or more fiducial markers 108. The fiducial markers 108 are formed from a radiopaque material, and thus permit identification of the IVUS imaging device in X-ray images.

In some examples, the matching of image intensity values determined at positions along the guidewire 104 in the X-ray image frame $105_{1 \ldots n}$, with an expected intensity pattern 107 representing the IVUS imaging device 102, includes using a machine learning algorithm that is trained to detect the IVUS imaging device 102. The machine learning algorithm may be trained to detect the IVUS imaging device 102 using training image data including a plurality of X-ray images representing the IVUS imaging device. The machine learning algorithm may for example include a support vector machine "SVM" algorithm, or another algorithm. When a machine learning algorithm is used to perform the matching in operation S120, the machine learning algorithm may identify one or more features of the IVUS imaging device such as its imaging portion 106, or it fiducial markers 108, as being characteristic of the IVUS imaging device, and base its matching on these features.

The expected intensity pattern 107 used in the operation S120 may be a one- or two-dimensional pattern. For example, if the IVUS imaging device 102 includes a radiopaque material, the expected intensity pattern 107 representing the IVUS imaging device 102 may include an X-ray attenuation pattern of the radiopaque material extending along an axial and/or a radial direction with respect to the guidewire 104.

In some examples, the expected intensity pattern 107 represents an expected separation between two or more of the radiopaque markers along the guidewire. In these examples the matching of image intensity values determined at positions along the guidewire 104 in the X-ray image frame $105_{1 \ldots n}$, with an expected intensity pattern 107 representing the IVUS imaging device 102; includes measuring a separation between two or more of the radiopaque markers along the guidewire, and comparing the measured separation with the expected separation.

In some examples, an X-ray attenuation pattern of the radiopaque material extending along an axial direction with respect to the guidewire 104 may be considered to represent a profile. In these examples, the matching of image intensity values determined at positions along the guidewire 104 in the X-ray image frame $105_{1 \ldots n}$, with an expected intensity pattern 107 representing the IVUS imaging device 102, includes:

determining the image intensity values at the positions along the guidewire 104 in the X-ray image frame $105_n$ by sampling the image intensity values within a window extending transversally with respect to the guidewire 104 to provide a composite value for the window, at each position; and comparing the composite values determined at the positions along the guidewire 104, with the expected intensity pattern 107 representing the IVUS imaging device 102, and wherein the expected intensity pattern 107 comprises an expected profile of the composite values along the length of the guidewire 104.

The window may have a predetermined length along the guidewire, such as one or more pixels in the X-ray image, and the composite value for the window may for example represent the average of the image intensity values within the window, or the maximum, or minimum of the image intensity values within the window. These examples are described in more detail with reference to FIG. 4 below.

In some examples, in operation S120, the expected intensity pattern 107 is translated along the guidewire 104 in order to determine a position of a match with the intensity values in the X-ray image $105_n$. In these examples, the operation of determining S120 a position of an imaging portion 106 of the IVUS imaging device 102 along the guidewire 104, includes translating the expected intensity pattern 107 representing the IVUS imaging device 102 along the guidewire 104 in the X-ray image frame $105_{1 \ldots n}$ in order to determine a position at which the image intensity values in the X-ray image frame $105_{1 \ldots n}$, match the expected intensity pattern 107 representing the IVUS imaging device 102.

Translating the expected intensity pattern 107 along the guidewire that is identified in operation S110, may be considered to improve the speed of determining the position of the match because the guidewire localises the search region within the X-ray image frame. The expected intensity pattern 107 may be translated along the guidewire by for example stepping its position along the guidewire in steps of one or more pixels, or by another step size, and determining whether a match exists at each step.

Another example of matching of image intensity values determined at positions along the guidewire 104 in the X-ray image frame $105_{1 \ldots n}$, with an expected intensity pattern 107 representing the IVUS imaging device 102, that is performed in the operation S120, is described with reference to FIG. 3 and FIG. 4.

Figures 3A, 3B, 3C, 3D:
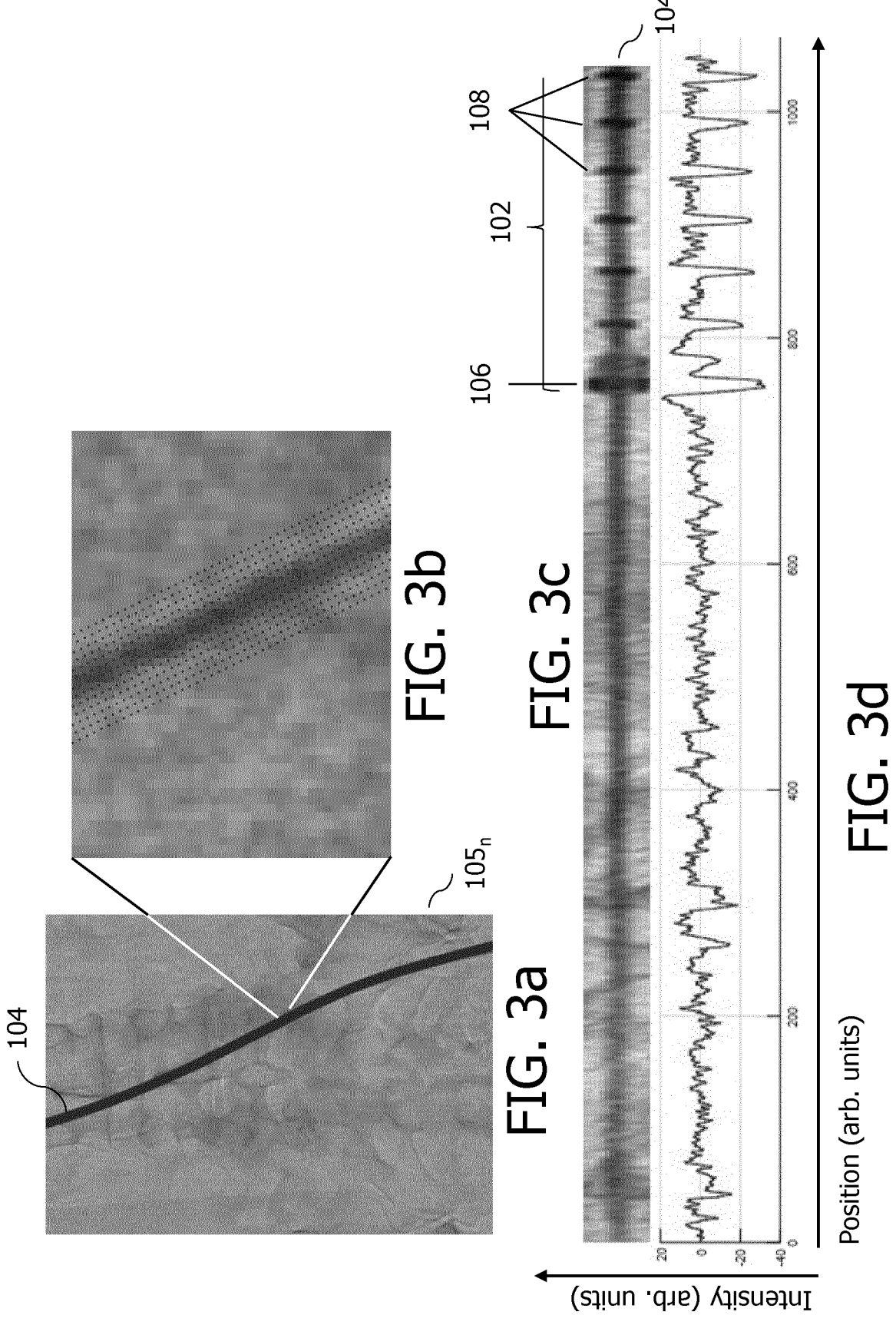
FIG. 3 illustrates a) an X-ray image frame $105_n$ including a guidewire 104, b) the sampling of image intensity values in the X-ray image frame $105_n$ at a predetermined spatial resolution c) the result of sampling the image intensity values in an X-ray image frame $105_n$ with a predetermined spatial resolution in b), and d) the average image intensity values determined at positions along the guidewire 104 in the X-ray image frame $105_n$, and which are obtained by averaging the sampled image intensity values obtained from c) within a window extending transversally with respect to the guidewire 104, in accordance with some aspects of the present disclosure.

FIG. 3 illustrates a) an X-ray image frame $105_n$ including a guidewire 104, b) the sampling of image intensity values in the X-ray image frame $105_n$ at a predetermined spatial resolution c) the result of sampling the image intensity values in an X-ray image frame $105_n$ with a predetermined spatial resolution in b), and d) the average image intensity values determined at positions along the guidewire 104 in the X-ray image frame $105_n$, and which are obtained by averaging the sampled image intensity values obtained from c) within a window extending transversally with respect to the guidewire 104, in accordance with some aspects of the present disclosure. In FIG. 3a, the guidewire has been identified in the X-ray image frame $105_n$ in operation S110, for example using the image segmentation techniques described above.

In FIG. 3b, the image intensity values in the X-ray image frame $105_n$ are sampled using a predetermined resolution. The samples are indicated by a grid of black dots in FIG. 3b. The sampling resolution used in sampling the X-ray image $105_n$ illustrated in FIG. 3b has a fixed step size in each of two orthogonal directions. Samples of the X-ray image intensity values are obtained by overlaying the grid on the guidewire and determining the intensity values at the points of intersection of the grid and the guidewire. The grid extends along the guidewire in a length direction and has a fixed height in a direction that is orthogonal to the guidewire. The height is sufficient to overlap the guidewire and the interventional device.

The result of the sampling in FIG. 3b is illustrated in FIG. 3c, in the form of image intensities along a straightened-out guidewire 104. The IVUS imaging device 102, including the imaging portion 106, is visible towards the right-hand side of FIG. 3c. Next, composite values representing the sampled pixel intensities along the guidewire 104 in the X-ray image frame $105_n$, are determined by averaging the sampled image intensity values within a window extending transversely with respect to the guidewire 104. In the illustrated example, the window extends transversely in an orthogonal direction with respect to the guidewire and on both sides of the guidewire 104. The window has a predetermined length along the length of the guidewire. These composite values are illustrated in FIG. 3d at positions, i.e. "position (arb. units)", along the guidewire. It is noted that the composite value for the window may alternatively be computed using another metric than the average value. For example, the composite value may represent the maximum value, or the minimum value, within the window. Windows with a different length along the guidewire, a different window step size, and windows with a different transverse extent, may alternatively be used to compute the composite values.

Having determined the image intensity values at the positions along the guidewire 104 in the X-ray image frame $105_n$ by sampling the image intensity values within a window extending transversally with respect to the guidewire 104 to provide a composite value for the window, at each position; next the composite values determined at the positions along the guidewire 104, are compared with an expected intensity pattern 107 representing the IVUS imaging device 102. In one example, the expected intensity pattern 107 comprises an expected profile of the composite values along the length of the guidewire 104. This is illustrated with reference to FIG. 4, which illustrates a) image intensities from an X-ray image frame $105_n$ including a guidewire 104 and an IVUS imaging device 102, b) a first example of an expected intensity pattern 107 representing a portion of the IVUS imaging device 102, and c) a second example of an expected an expected intensity pattern 107 representing a portion of the IVUS imaging device 102, in accordance with some aspects of the present disclosure.

FIG. 4a corresponds to a portion of FIG. 3c, i.e. it represents the result of sampling the image intensity values in the X-ray image frame $105_n$ with a predetermined spatial resolution. FIG. 4c illustrates by way of the intensity values marked with an "X", an expected intensity pattern 107 representing a portion of the IVUS imaging device 102. It is noted that the scale of FIG. 4c is expanded with respect to FIG. 4a in order to illustrate detail along the length of the guidewire. The expected intensity pattern 107 represents the separation between the expected peak intensity values along the guidewire. The separations, and optionally their peak intensity values, are characteristic of the IVUS imaging device 102. In the illustrated example, the highest intensity peak from these peaks is indicative of the position of the imaging portion 106 of the IVUS imaging device 102. The continuous curve in FIG. 4c represents the intensity values that are determined from the image intensities in FIG. 4a using the windowing and averaging operations that were described with reference to FIG. 3c and FIG. 3d. In FIG. 4c, a match can be seen to exist between the peak intensity values of the continuous curve in FIG. 4c, and the expected intensity pattern 107. Thus, the position of the highest peak from these peaks identifies the position of the imaging portion 106 of the IVUS imaging device 102 along the guidewire 104.

By using the separations between the peaks of the intensity values as the expected intensity pattern 107, a fast determination of the position of the IVUS imaging device along the guidewire, can be provided with modest processing resources. This is particularly advantageous when the method is used during live X-ray imaging.

In other examples, rather than using separations and/or the intensity values at the peaks of the intensity values as characteristic of the IVUS imaging device, other characteristics of the intensity values, and characteristics from other portions of the IVUS imaging device may alternatively be used to determine the position of an imaging portion 106 of the IVUS imaging device 102 along the guidewire 104. For example, the minimum intensity values may be used additionally or alternatively to the maximum intensity values. Alternatively, a continuous curve representing the intensity values of the IVUS imaging device along the guidewire may be used. Alternatively, the expected intensity pattern 107 for the fiducial markers may be used. Alternatively, the expected intensity pattern 107 for the fiducial markers may be used in combination with an expected distance between the fiducial markers. Knowledge of the spatial separation between the imaging portion 106 of the IVUS imaging device 102 and the fiducial markers may also be used to predict the position of the imaging portion 106 relative to the fiducial markers. A combination of these approaches may also be used.

In yet another example, the expected intensity pattern 107 representing the IVUS imaging device 102 comprises an X-ray attenuation pattern of the radiopaque material extending along an axial and a radial direction with respect to the guidewire 104. This is illustrated in FIG. 4b, wherein a template expected intensity pattern 107 is used to determining S120 a position of an imaging portion 106 of the IVUS imaging device 102 along the guidewire 104, by matching image intensity values determined at positions along the guidewire 104 in the X-ray image frame $105_{1 \ldots n}$, with the template expected intensity pattern 107.

In some examples, the position of the imaging portion 106 of the IVUS imaging device 102 along the guidewire 104 is determined in operation S120 by performing an initial translation of the expected intensity pattern 107 along the guidewire 104, and then performing a subsequent translation of the expected intensity pattern 107. The initial translation provides an estimated position of the imaging portion 106 of the IVUS imaging device 102 along the guidewire 104, and the subsequent translation provides a more accurate position. In some examples, both the initial translation and the subsequent translation are performed using the expected intensity pattern 107 of the fiducial markers 108 coupled to the IVUS imaging device 102. In some examples, both the initial translation and the subsequent translation are performed using the expected intensity pattern 107 of the imaging portion 106 of the IVUS imaging device 102. In some examples, the initial translation may be performed using the expected intensity pattern 107 of the fiducial markers 108 coupled to the IVUS imaging device 102, and the subsequent translation may be performed using the expected intensity pattern 107 of the imaging portion 106 of the IVUS imaging device 102. In some examples, the initial translation and the subsequent translation may be performed with different resolution, or step size. For example, the step size of the subsequent translation may be smaller than the steps size used in the initial translation. Generating an initial estimated position, and then a more accurate position in this manner may permit a determination of the position of the imaging portion of the IVUS imaging device that is both fast and accurate.

In another example, the operation of translating the expected intensity pattern 107 representing the IVUS imaging device 102 along the guidewire 104 in the X-ray image frame $105_{1 \ldots n}$ in order to determine a position at which the image intensity values in the X-ray image frame $105_{1 \ldots n}$, match the expected intensity pattern 107 representing the IVUS imaging device 102, comprises:

performing an initial translation of the expected intensity pattern 107 representing the IVUS imaging device 102 along the guidewire 104 in the X-ray image frame $105_{1 \ldots n}$ by sampling the image intensity values in the X-ray image frame $105_{1 \ldots n}$ with a first spatial resolution, to determine a first estimated position of the imaging portion 106 of the IVUS imaging device 102 along the guidewire 104;

estimating a scale factor for at least a portion of the IVUS imaging device based on the sampled image intensity values and a known dimension of the portion of the IVUS imaging device; and performing a subsequent translation of the expected intensity pattern 107 representing the IVUS imaging device 102 along the guidewire 104 in the X-ray image frame $105_{1 \ldots n}$ by sampling the image intensity values in the X-ray image frame $105_{1 \ldots n}$ with a second spatial resolution, to determine a second estimated position of the imaging portion 106 of the IVUS imaging device 102 along the guidewire 104, the second spatial resolution being adjusted based on the estimated scale factor; and using the second estimated position as the determined position of the imaging portion 106 of the IVUS imaging device 102 along the guidewire 104.

The scale factor represents a ratio of a measurement in the X-ray image to a real-world metric. For example, it may represent a number of samples, or a number of pixels, in the X-ray image per unit of length. It may for example represent a number of pixels in the X-ray image $105_n$ per centimetre, wherein the real-world centimetre dimension is known from a separation between two fiducial markers coupled to the shaft of the IVUS imaging device that is visualised in the X-ray image $105_n$. The known separation may be provided by a manufacturer specification. By way of an example, in the aforementioned Visions PV.035® catheter, the separation between adjacent fiducial makers is specified as 10 millimetres. If, in this example, the number of pixels per centimetre is determined from the X-ray image frame to be less than or equal to a predetermined threshold during the initial translation, the second spatial resolution, or step size, used in the sampling, may be changed, for example it may be decreased, so as to provide a more accurate determination of the second estimated position of the imaging portion 106 of the IVUS imaging device 102 along the guidewire 104. The second spatial resolution may for example be adjusted based on the estimated scale factor, so as to provide a desired scale factor in the subsequent translation. In so doing, the position of the IVUS imaging device may be determined with a repeatable accuracy.

In another example, the image intensity values in the X-ray image frame $105_{1 \ldots n}$ are initially sampled with a first spatial resolution, and subsequently sampled with a second spatial resolution, in order to determine a position at which the image intensity values in the X-ray image frame, match the expected intensity pattern 107 representing the IVUS imaging device 102. The spatial resolution represents a number of samples per unit of length or area in the X-ray image. The spatial resolution affects the accuracy of determining the position. In this example, the first spatial resolution is used to determine the position of the fiducial markers, and also to estimate a separation between the fiducial markers. An approximate position of the imaging portion of the IVUS imaging device is also inherently determined from the sampling that is performed with the first spatial resolution. The second spatial resolution is determined based on the estimated separation between the fiducial markers 108. The second spatial resolution is used to determine a position at which the image intensity values in the X-ray image frame, match the expected intensity pattern 107 representing the IVUS imaging device 102. The second spatial resolution may be used to determine the position of the imaging portion 106 of the IVUS imaging device 102. The second spatial resolution may be higher than the first spatial resolution. Advantageously the first spatial resolution may provide a first approximate position of the IVUS imaging device, and the second spatial resolution may provide a more accurate determination of the position of the imaging portion of the IVUS imaging device.

In this example, the IVUS imaging device 102 includes a plurality of fiducial markers 108 that are coupled to the IVUS imaging device 102 and distributed axially along the guidewire 104. The operation of determining S120 a position of an imaging portion 106 of the IVUS imaging device 102 along the guidewire 104, includes:

identifying positions of the fiducial markers 108 along the guidewire 104 by sampling the image intensity values in the X-ray image frame $105_{1 \ldots n}$ with a first spatial resolution;

computing an estimated separation between at least one pair of the fiducial markers 108 based on the identified positions of the fiducial markers 108; and sampling the image intensity values in the X-ray image frame $105_{1 \ldots n}$ with a second spatial resolution, to determine a position at which the image intensity values in the X-ray image frame, match the expected intensity pattern 107 representing the IVUS imaging device 102, and wherein the second spatial resolution is determined based on the estimated separation between at least one pair of the fiducial markers 108 and a known separation between the at least one pair of the fiducial markers.

In this example, the estimated separation between the fiducial markers may be determined in terms of a number of X-ray image pixels, or a physical measurement on the X-ray image. The known separation between the fiducial markers may be known from a manufacturer specification. For example, the fiducial markers 108 coupled to the shaft of some IVUS imaging catheters have a separation of 10 millimetres.

In another example the position of the imaging portion 106 of the IVUS imaging device 102 along the guidewire 104 is determined using a template pattern. FIG. 5 illustrates an example of a template pattern 109 representing an imaging portion 106 of the IVUS imaging device 102, in accordance with some aspects of the present disclosure. The template pattern illustrated in FIG. 5 represents a two-dimensional X-ray image of the imaging portion 106 of the IVUS imaging device 102 and extends in an axial direction and in a radial direction with respect to the guidewire 104. In this example, the position of the imaging portion 106 of the IVUS imaging device 102 along the guidewire 104 is determined in the plurality of X-ray image frames $105_{1 \ldots n}$ in accordance with operation S120 that was described above with reference to FIG. 2. The position of the imaging portion 106 may be determined from the operation S120 based on an identification of the fiducial markers in the X-ray image frames $105_{1 \ldots n}$. For example, it may be assumed that the imaging portion 106 is located towards the rear end of the fiducial markers 109 during a pullback operation. Next, a template pattern 109 is generated. The template pattern 109 represents the imaging portion 106 of the IVUS imaging device 102, and is generated by averaging the image intensity values surrounding the determined position of the imaging portion 106 of the IVUS imaging device 102 in the plurality of X-ray image frames $105_{1 \ldots n}$. Next, the operation S120 is repeated, this time, determining S120 a position of an imaging portion 106 of the IVUS imaging device 102 along the guidewire 104 for the plurality of X-ray image frames $105_{1 \ldots n}$, using the template pattern as the expected intensity pattern 107 representing the IVUS imaging device 102. This provides an adjusted position of the imaging portion 106 of the IVUS imaging device 102 along the guidewire 104 in each X-ray image frame $105_{1 \ldots n}$.

The adjusted position that is determined in this example may be considered to provide an accurate determination of the position of the imaging portion of the IVUS imaging device. This is because the averaging operation provides an accurate representation of the shape of the imaging portion 106 of the IVUS imaging device 102.

In accordance with another example, a scale factor for the guidewire is determined. As mentioned above, in some examples the scale factor is determined subsequent to operation S120, i.e. subsequent to the determining S120 a position of an imaging portion 106 of the IVUS imaging device 102 along the guidewire 104. However, the scale factor may be determined in X-ray imaging procedures when imaging elongate interventional devices in general, and its determination is therefore not limited to use in combination with an IVUS imaging procedure. Examples wherein a scale factor is determined, may therefore be performed independently of the operations S120 and S130.

In accordance with one example, the IVUS imaging device 102 includes a catheter having a shaft and a plurality of fiducial markers 108. The fiducial markers 108 are coupled to the catheter, and distributed axially along the shaft of the catheter. In this example, the plurality of fiducial markers 108 are identified in the X-ray image frame $105_{1 \ldots n}$. A scale factor for the portion of the guidewire 104 including the fiducial markers 108, is then determined based on a measured separation between two or more of the plurality of fiducial markers 108 identified in the X-ray image frame $105_{1 \ldots n}$ and a known separation between the two or more fiducial markers 108.

The scale factor thus represents a ratio of a measurement in the X-ray image to a real-world metric. For example, it may represent a number of pixels in the X-ray image $105_n$ per centimetre, or another unit of length. The real-world centimetre dimension may be known from a manufacturer specification of the separation between the fiducial markers coupled to the shaft of the IVUS imaging device.

Continuing with this example, the IVUS imaging device may also translated along the guidewire 104 between successive X-ray image frames $105_{1 \ldots n}$ in the temporal sequence in order to generate a combined scale factor 110 for the guidewire 104 that varies along its length. Here, the IVUS imaging device 102 is translated along the guidewire 104 between successive X-ray image frames $105_{1 \ldots n}$ in the temporal sequence. Scale factors for the portion of the guidewire 104 that include the fiducial markers 108 in each image frame, are combined for corresponding sections of the guidewire 104 in the X-ray image frames $105_{1 \ldots n}$, to provide a combined scale factor 110 for the guidewire 104 that varies along the length of the guidewire 104.

Figures 4, 5, 6:
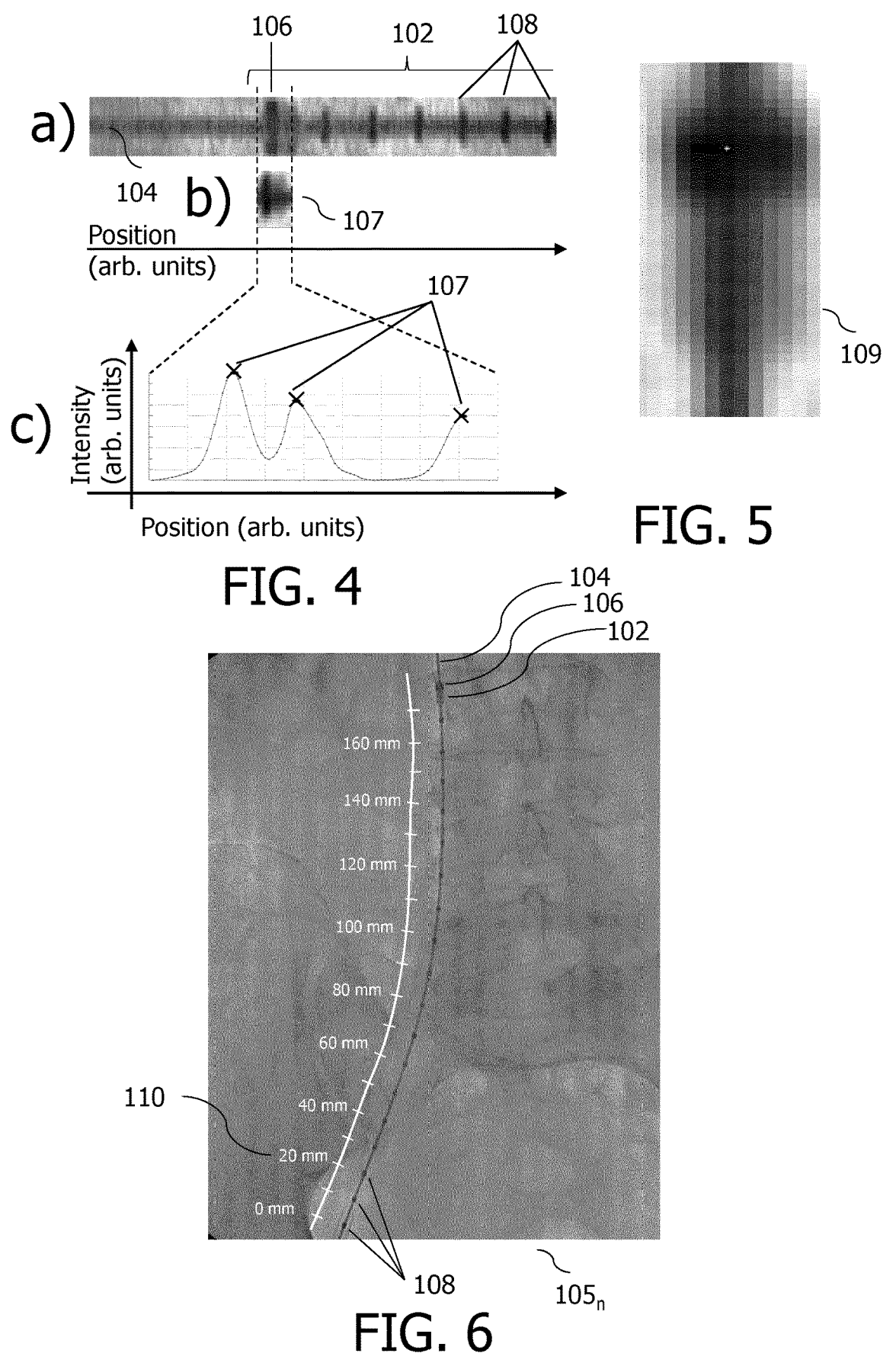

Thereto, FIG. 6 illustrates an example of an X-ray image frame $105_n$ including a guidewire 104 and a combined scale factor 110 for the guidewire 104 that varies along the length of the guidewire 104, in accordance with some aspects of the present disclosure. The example combined scale factor 110 illustrated in FIG. 6 is provided as a millimetre length scale along the length of the guidewire. It is noted that the combined scale factor, i.e. the number of X-ray image pixels representing each unit of length in the X-ray image, varies along the length of the guidewire 104. Since the scale factor varies along the length of the guidewire, it may be used to accurately determine a length along the guidewire. For example, the scale factor may be used to accurately determine a required length of a stent to be used in a peripheral venous intervention.

In some examples, the scale factors are combined to provide the combined scale factor 110. The combined scale factor may for example be determined by averaging the scale factors for corresponding sections of the guidewire. Alternatively, the scale factors for the portion of the guidewire including the fiducial markers in each image frame, may be combined for corresponding sections of the guidewire in the X-ray image frames by using a regularisation term to encourage a continuous change of scale factor along the length of the guidewire. In this example, multiple length measurements, each length measurement representing the separation between different combinations of pairs of markers in an X-ray image frame, are made in multiple X-ray image frames, and the multiple length measurements used to compose a system of equations (normally overdetermined) for the length as a function of position along guidewire. In order to increase robustness to possible sporadic inaccuracies in marker detection, the system of equations may be supplemented with a regularization term encouraging a smooth length change along the guidewire.

Clinical investigations often require the use of multiple guidewires, and the X-ray image frames $105_{1 \ldots n}$ may therefore include multiple guidewires. In some examples the guidewire that includes the IVUS imaging device is selected for use in the method. In accordance with these examples, the guidewire that is identified in the operation S110 may be identified as the guidewire that includes the fiducial markers

108 of the IVUS imaging device 102. In accordance with these examples, the X-ray image frames $105_{1 \ldots n}$ in the temporal sequence comprise a plurality of guidewires 104; and the identifying S110 the guidewire 104 in the X-ray image frame, includes:

identifying the fiducial markers 108 in the X-ray image frame; and selecting the guidewire 104 having the identified fiducial markers 108 distributed axially along its length.

Referring back to FIG. 2, having determined the position of the imaging portion 106 of the IVUS imaging device 102 along the guidewire 104, in operation S120, the method continues with operation S130, i.e. mapping S130 a position of an IVUS image frame $101_{1 \ldots m}$ generated contemporaneously with the X-ray image frame $105_{1 \ldots n}$, to the determined position along the guidewire 104.

In some examples, IVUS imaging frames may be generated in synchronisation with the X-ray image frames, and therefore the contemporaneous IVUS and X-ray image frames may be readily identified. In other examples, the contemporaneous IVUS and X-ray image frames may be identified as image frames from the respective sequences that occur closest in time to each other. The timing of the respective image frames may be determined from their position in the temporal sequence, or from timestamps indicative of the time of their generation.

The use of various techniques is contemplated in the mapping operation performed in operation S130. In general, images representing the contemporaneous IVUS and X-ray image frames may be displayed simultaneously. In one example, the operation S130, i.e. the mapping S130 a position of an IVUS image frame $101_{1 \ldots m}$ generated contemporaneously with the X-ray image frame $105_{1 \ldots n}$, to the determined position along the guidewire 104, includes:

displaying a first image representing one or more of the X-ray image frames $105_{1 \ldots n}$ in the temporal sequence and the guidewire 104, and simultaneously displaying a second image representing an IVUS image frame from the temporal sequence of IVUS image frames $101_{1 \ldots m}$; and indicating the mapped position of the IVUS image frame along the guidewire 104 in the first image.

The displayed IVUS image may represent a planar slice through the vasculature. In general, the position may be mapped by displaying a marker indicating the position of the IVUS image in the X-ray image, or by highlighting the respective position in the X-ray image in a different manner, such as by using a change in colour or intensity in the X-ray image. In some examples, the position of the guidewire 104 in the first image, is determined by averaging the position of the guidewire 104 identified in the X-ray image frames $105_{1 \ldots n}$.

Figure 7:
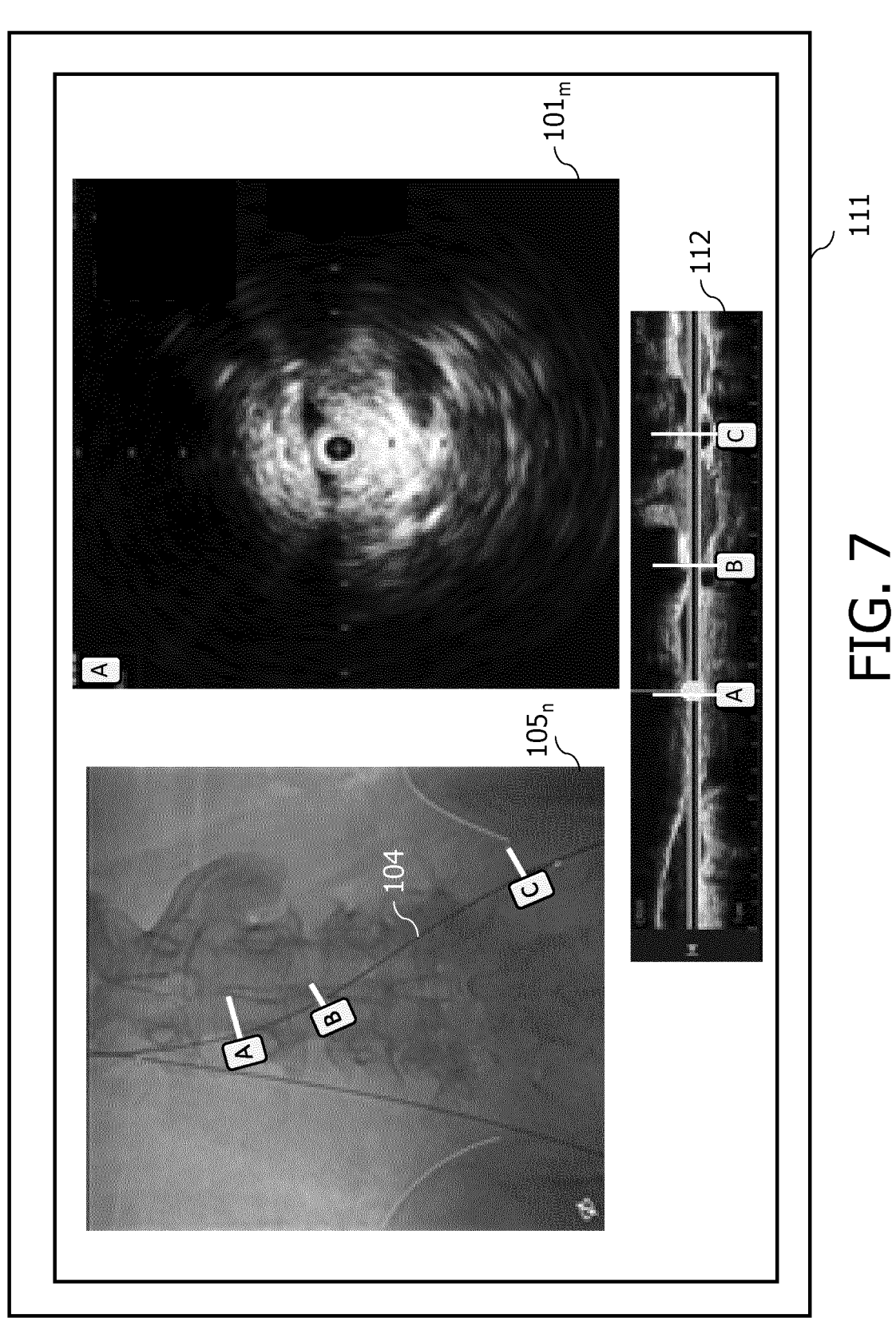
FIG. 7 illustrates an example of a display 111 that includes a mapping of a position of an IVUS image frame $101_m$ to a position along a guidewire 104 in an X-ray image $105_n$, in accordance with some aspects of the present disclosure.

FIG. 7 illustrates an example of a display 111 that includes a mapping of a position of an IVUS image frame $101_m$ to a position along a guidewire 104 in an X-ray image $105_n$, in accordance with some aspects of the present disclosure. In the illustrated example, the displayed IVUS image frame $101_m$ is labelled "A" and is mapped to the position "A" on the guidewire 104 in the X-ray image frame 105n by means of the corresponding "A" markers. The display 111 also includes an In-Line Digital, or Image Longitudinal Display "ILD" view 112 showing a cross sectional view of the IVUS image frames $101_{1 \ldots m}$, and which form a cross-sectional image along a length of the vasculature along which the IVUS imaging device has been translated. The ILD view 112 may be used by a medical practitioner to navigate the IVUS imaging device along the lumen during a pullback procedure. If the correct cross sectional angle, sometimes referred to as a clock angle, is used, useful clinical information such as side branches of the vessel or lumen, can be identified. The position of the IVUS image labelled A, as well as the positions of two further images "B" and "C", are indicated on the ILD view 112, as well as on the guidewire 104 in the X-ray image frame $105_n$. The displayed X-ray image $105_n$ represents one or more of the X-ray image frames $105_{1 \ldots n}$ in the temporal sequence of X-ray images. The displayed X-ray image $105_n$ may for example be a selected one of the X-ray image frames $105_{1 \ldots n}$, or a composite image generated from multiple of the X-ray image frames $105_{1 \ldots n}$, or it may be an X-ray image generated before or after the temporal sequence of X-ray images, and therefore represent a similar view of the guidewire 104.

In so doing, the guidewire 104 provides a roadmap of the vasculature, and the markers "A" indicate the corresponding position of the IVUS image $101_m$, also labelled "A", along the guidewire 104 in the X-ray image $105_n$. Providing the roadmap of the vasculature in this manner obviates the need for a venogram and its associated contrast agent. Instead, the guidewire 108 acts as the roadmap. This helps to reduce contrast injection and X-ray dose to the patient.

Figure 8:
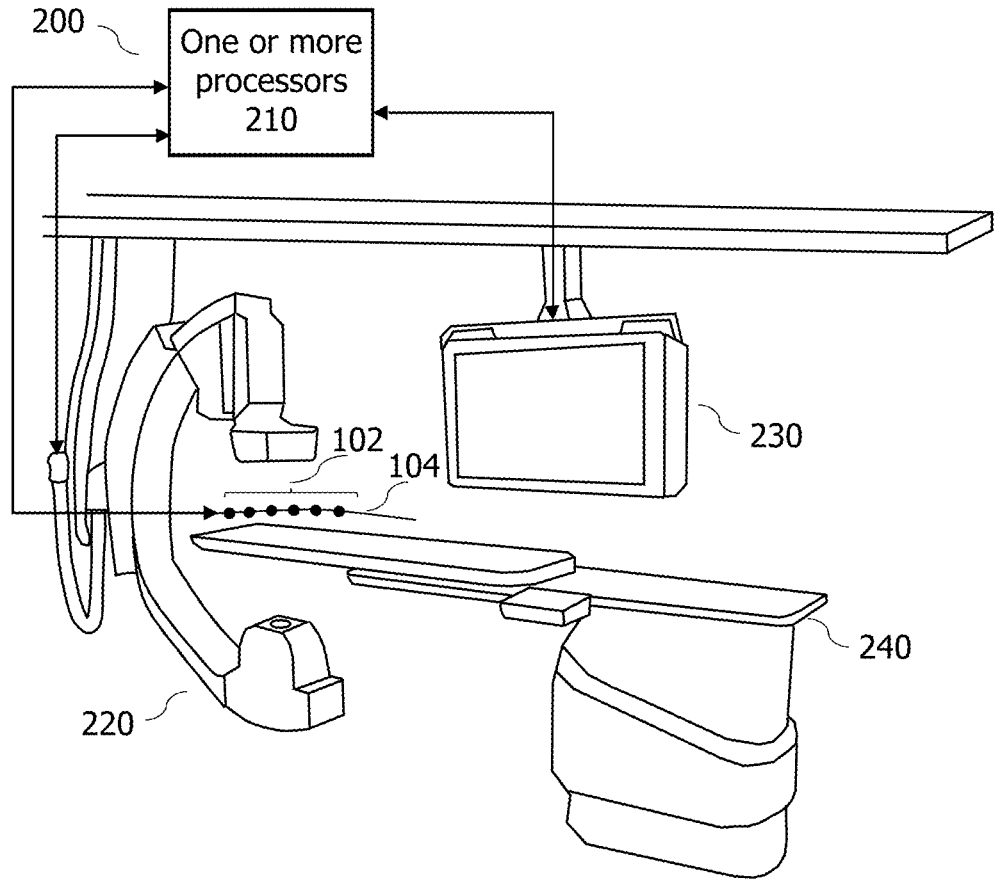
FIG. 8 is a schematic illustration of an example system 200 for registering positions of a temporal sequence of IVUS image frames $101_{1 \ldots m}$ generated by an IVUS imaging device 102 coupled to a guidewire 104, to positions along the guidewire 104 in a temporal sequence of X-ray image frames $105_{1 \ldots n}$, in accordance with some aspects of the present disclosure.

FIG. 8 is a schematic illustration of an example system 200 for registering positions of a temporal sequence of IVUS image frames $101_{1 \ldots m}$ generated by an IVUS imaging device 102 coupled to a guidewire 104, to positions along the guidewire 104 in a temporal sequence of X-ray image frames $105_{1 \ldots n}$, in accordance with some aspects of the present disclosure. The system 200 for registering positions of a temporal sequence of intravascular ultrasound, IVUS, image frames $101_{1 \ldots m}$ generated by an IVUS imaging device 102 coupled to a guidewire 104, to positions along the guidewire 104 in a temporal sequence of X-ray image frames $105_{1 \ldots n}$ including the IVUS imaging device 102 and the guidewire 104, comprises one or more processors 210 configured to perform a method comprising: for a plurality of X-ray image frames $105_{1 \ldots n}$ in the temporal sequence:

identifying S110 the guidewire 104 in the X-ray image frame;

determining S120 a position of an imaging portion 106 of the IVUS imaging device 102 along the guidewire 104, based on a matching of image intensity values determined at positions along the guidewire 104 in the X-ray image frame $105_{1 \ldots n}$ with an expected intensity pattern 107 representing the IVUS imaging device 102; and mapping S130 a position of an IVUS image frame $101_{1 \ldots m}$ generated contemporaneously with the X-ray image frame $105_{1 \ldots n}$, to the determined position along the guidewire 104.

It is noted that the one or more processors 210 of the system 200 may also incorporate one or more features described above in relation to the method. These are not duplicated here, for the sake of brevity. The system 200 may also incorporate one or more of the X-ray imaging system 220, the display 230, and the patient bed 240, as illustrated in FIG. 8.

As mentioned above, the method of determining the scale factor may be used in X-ray imaging procedures in general, and is not limited to use in combination with IVUS imaging procedures. The scale factor may be determined during X-ray imaging procedures when a plurality of fiducial markers 108 are translated along the axis of an elongate interventional device. The method of determining the scale factor is therefore not limited to use with fiducial markers disposed on an IVUS imaging device.

In accordance with one example, a computer-implemented method of determining an X-ray image scale factor that varies along an axis of an elongate interventional device during a procedure wherein a plurality of fiducial markers 108 are translated along the axis of the elongate interventional device. The method comprises:

receiving a temporal sequence of X-ray image frames $105_{1 \ldots n}$ representing the elongate interventional device and the fiducial markers 108 whilst the fiducial markers 108 are translated along the axis of the elongate interventional device; and for a plurality of X-ray image frames $105_{1 \ldots n}$ in the temporal sequence:

identifying the elongate interventional device and the fiducial markers 108 in the X-ray image frame;

determining a scale factor for the portion of the elongate interventional device including the fiducial markers 108 based on a measured separation between two or more of the plurality of markers 108 identified in the X-ray image frame $105_{1 \ldots n}$ and a known separation between the two or more fiducial markers 108; and combining the scale factors for the portion of the elongate interventional device including the fiducial markers 108 in the X-ray image frame $105_{1 \ldots n}$ for corresponding sections of the elongate interventional device in the X-ray image frames $105_{1 \ldots n}$, to provide the X-ray image scale factor that varies along the axis of the elongate interventional device.

The elongate interventional device may for example be a guidewire, a catheter, a balloon delivery system with multiple radiopaque markers, or another elongate interventional device along which fiducial markers, are translated during a medical intervention. The fiducial markers may be coupled to an IVUS imaging device, or to another device such as an OCT imaging device, a pressure sensing device, an ICE catheter, a blood flow measurement device, a stent insertion device, or a vascular treatment device such as an atherectomy device.

In accordance with another example, in the computer-implemented method of determining an X-ray image scale factor that varies along an axis of an elongate interventional device, the operation of combining the scale factors for the portion of the elongate interventional device including the fiducial markers 108 in the X-ray image frame $105_{1 \ldots n}$ for corresponding sections of the elongate interventional device in the X-ray image frames $105_{1 \ldots n}$, comprises:

using a regularisation term to encourage a continuous change of the X-ray image scale factor along the length of the elongate interventional device.

In accordance with another example, the elongate interventional device comprises a guidewire 104, and the procedure wherein a plurality of fiducial markers 108 are translated along the axis of the elongate interventional device comprises an IVUS pullback procedure, and the fiducial markers 108 are coupled to an IVUS imaging catheter configured to generate IVUS image frames $101_{1 \ldots m}$ during the IVUS pullback procedure.

The above examples are to be understood as illustrative of the present disclosure and not restrictive. Further examples are also contemplated. For instance, the examples described in relation to the computer-implemented method, may also be provided by the computer program product, or by the computer-readable storage medium, or by the system 200, in a corresponding manner. It is to be understood that a feature described in relation to any one example may be used alone, or in combination with other described features, and may also be used in combination with one or more features of another of the examples, or a combination of other examples. Furthermore, equivalents and modifications not described above may also be employed without departing from the scope of the invention, which is defined in the accompanying claims. In the claims, the word "comprising" does not exclude other elements or operations, and the indefinite article "a" or "an" does not exclude a plurality. The mere fact that certain features are recited in mutually different dependent claims does not indicate that a combination of these features cannot be used to advantage. Any reference signs in the claims should not be construed as limiting their scope.

The invention claimed is:

1. A system for registering positions of a temporal sequence of intraluminal sensing device data generated by an intraluminal sensing device to positions along a guidewire in a temporal sequence of extraluminal image frames including the intraluminal sensing device and the guidewire, wherein, wherein the intraluminal sensing device comprises a plurality of radiopaque markers, wherein the system comprises one or more processors configured to:

identify the guidewire in an extraluminal image frame;

identify positions of the plurality of radiopaque markers along the guidewire by sampling a first set of image intensity values in the extraluminal image frame with a first spatial resolution;

compute an estimated separation between at least one pair of the plurality of radiopaque markers based on the identified positions of the plurality of radiopaque markers;

sample the first set of image intensity values in the extraluminal image frame with a second spatial resolution, to determine a matching between the first set of image intensity values and a second set of image intensity values known to represent a portion of the intraluminal sensing device, wherein the second spatial resolution is determined based on the estimated separation and a known separation between the at least one pair, determine a position of a sensing portion of the intraluminal sensing device along the guidewire, based on the matching; and map a position of intraluminal sensing device data generated contemporaneously with the extraluminal image frame to the determined position.

2. The system of claim 1, wherein the second set of image intensity values is known to represent the sensing portion of the intraluminal sensing device.

3. The system of claim 1, wherein the temporal sequence of intraluminal sensing device data comprises a temporal sequence of intraluminal image frames.

4. The system of claim 3, wherein the intraluminal ultrasound image frames comprise intravascular ultrasound image frames or endobronchial ultrasound image frames.

5. The system of claim 3, wherein the temporal sequence of extraluminal image frames comprise radiographic image frames.

6. A computer-implemented method of registering positions of a temporal sequence of intraluminal sensing device data generated by an intraluminal sensing device to positions along a guidewire in a temporal sequence of extraluminal image frames including the intraluminal sensing device and the guidewire, wherein the intraluminal sensing device comprises a plurality of radiopaque markers, wherein the method comprises:

identifying the guidewire in an extraluminal image frame;

identifying positions of the plurality of radiopaque markers along the guidewire by sampling a first set of image intensity values in the extraluminal image frame with a first spatial resolution;

computing an estimated separation between at least one pair of the plurality of radiopaque markers based on the identified positions of the plurality of radiopaque markers;

sampling the first set of image intensity values in the extraluminal image frame with a second spatial resolution, to determine a matching between the first set of image intensity values and a second set of image intensity values known to represent a portion of the intraluminal sensing device, wherein the second spatial resolution is determined based on the estimated separation and a known separation between the at least one pair, determining a position of a sensing portion of the intraluminal sensing device along the guidewire, based on the matching; and mapping a position of intraluminal sensing device data generated contemporaneously with the extraluminal image frame to the determined position along the guidewire.

7. The computer-implemented method of claim 6, wherein the second set of image intensity values is known to represent the sensing portion of the intraluminal sensing device, wherein the intraluminal sensing device comprises an intravascular imaging device or an endobronchial imaging device, wherein the temporal sequence of intraluminal sensing device data comprises a temporal sequence of intraluminal image frames provided by the intravascular imaging device or the endobronchial imaging device, wherein the temporal sequence of extraluminal image frames comprise radiographic image frames.

8. The computer-implemented method according to claim 7, wherein the intravascular imaging device comprises an intravascular ultrasound (IVUS) imaging device, wherein the radiographic image frames comprise X-ray image frames obtained from an X-ray imaging device and the temporal sequence of intraluminal image frames comprise IVUS image frames obtained from the IVUS imaging device.

9. The computer-implemented method according to claim 6, wherein the matching comprises:

sampling the first set of image intensity values within a window extending transversally with respect to the guidewire to provide a composite value for the window, at each position; and comparing the composite values determined at the positions along the guidewire, with the second set of image intensity values, and wherein the second set of image intensity values comprises an expected profile of the composite values along the guidewire.

10. The computer-implemented method according to claim 8, wherein the second set of image intensity values is known to represent an imaging portion of the IVUS imaging device, wherein determining the position of the sensing portion of the intraluminal sensing device comprises determining a position of the imaging portion of the IVUS imaging device.

11. The computer-implemented method according to claim 6, wherein the radiopaque markers are coupled to the intraluminal sensing device and are distributed axially along the guidewire.

12. The computer-implemented method according to claim 6, comprising:

generating a template pattern representing the sensing portion of the intraluminal sensing device by averaging the first set of image intensity values surrounding the determined position; and repeating determining the position of the sensing portion of the intraluminal sensing device along the guidewire for the temporal sequence of extraluminal image frames, using the template pattern, to provide an adjusted position of the sensing portion of the intraluminal sensing device along the guidewire in each extraluminal image frame.

13. The computer-implemented method according to claim 6, wherein the second set of image intensity values comprises an X-ray attenuation pattern of the plurality of radiopaque markers extending along an axial direction and/or a radial direction with respect to the guidewire.

14. The computer-implemented method according to claim 6, wherein the intraluminal sensing device comprises a catheter having a shaft, wherein the plurality of radiopaque markers are coupled to the catheter and distributed axially along the shaft of the catheter, and wherein the method comprises:

identifying the plurality of radiopaque markers in the extraluminal image frame; and determining a scale factor based on the estimated separation and the known separation.

* * * * *